(12) United States Patent
Bradford

(10) Patent No.: US 10,400,647 B2
(45) Date of Patent: Sep. 3, 2019

(54) METHOD FOR UREA CONVERSION EFFICIENCY MEASUREMENT

(71) Applicant: Tenneco Automotive Operating Company Inc., Lake Forest, IL (US)

(72) Inventor: Michael C. Bradford, Chelsea, MI (US)

(73) Assignee: Tenneco Automotive Operating Company Inc., Lake Forest, IL (US)

( * ) Notice: Subject to any disclaimer, the term of this patent is extended or adjusted under 35 U.S.C. 154(b) by 59 days.

(21) Appl. No.: 15/874,358

(22) Filed: Jan. 18, 2018

(65) Prior Publication Data

US 2018/0209319 A1    Jul. 26, 2018

Related U.S. Application Data

(60) Provisional application No. 62/448,425, filed on Jan. 20, 2017.

(51) Int. Cl.
*F01N 3/20* (2006.01)
*G01N 21/65* (2006.01)
(Continued)

(52) U.S. Cl.
CPC .............. *F01N 3/2066* (2013.01); *C01B 4/00* (2013.01); *C07B 33/00* (2013.01); *C07B 59/001* (2013.01);
(Continued)

(58) Field of Classification Search
CPC ............. F01N 3/2066; F01N 2560/026; F01N 2610/02; F01N 2900/1402;
(Continued)

(56) References Cited

U.S. PATENT DOCUMENTS

| 4,990,780 | A | * | 2/1991 | Lee | ................. | G01N 21/39 |
| | | | | | | 250/339.13 |
| 8,232,104 | B1 | * | 7/2012 | Frazier | ............. | C06B 23/008 |
| | | | | | | 436/164 |

(Continued)

FOREIGN PATENT DOCUMENTS

| DE | 102005034454 A1 | * | 3/2006 | ............ | G01F 1/704 |
| DE | 102015007554 A1 | * | 12/2016 | ......... | G01F 25/0007 |

(Continued)

OTHER PUBLICATIONS

International Search Report and Written Opinion from related PCT/US2018/014410 dated Jun. 207, 2018.

*Primary Examiner* — Audrey K Bradley
(74) *Attorney, Agent, or Firm* — Harness, Dickey & Pierce, P.L.C.

(57) ABSTRACT

A method and system for characterizing a chemical reaction in an exhaust after-treatment system that includes providing a first molecule that includes a chemical element that is isotopically labelled. The isotopically labelled first molecule is injected into an exhaust stream of the exhaust after-treatment system to supply the isotopically labelled first molecule to an exhaust treatment component, and second molecules including the chemical element that is isotopically labelled that are produced through a chemical reaction of the first molecule with other constituents of the exhaust stream are quantified.

20 Claims, 5 Drawing Sheets

(51) Int. Cl.
*G01N 30/72* (2006.01)
*C01B 4/00* (2006.01)
*C07B 59/00* (2006.01)
*C07B 33/00* (2006.01)
*G01N 21/3504* (2014.01)

(52) U.S. Cl.
CPC .......... *G01N 30/72* (2013.01); *C07B 2200/05* (2013.01); *F01N 2610/02* (2013.01); *F01N 2900/1402* (2013.01); *F01N 2900/1621* (2013.01); *G01N 21/3504* (2013.01); *G01N 21/65* (2013.01); *Y02T 10/24* (2013.01)

(58) Field of Classification Search
CPC ........................ F01N 2900/1621; G01N 21/65; G01N 30/72; C07B 2200/05; C01B 4/00
See application file for complete search history.

(56) References Cited

U.S. PATENT DOCUMENTS

| 8,381,512 | B2 | 2/2013 | Brinkman et al. |
| 9,238,984 | B2 | 1/2016 | Chavannavar |
| 2006/0237640 | A1* | 10/2006 | Delvigne ............ G01M 15/102 250/288 |
| 2007/0071666 | A1* | 3/2007 | Larsen .................. B01J 29/035 423/351 |
| 2012/0222404 | A1 | 9/2012 | Charial et al. |
| 2016/0356703 | A1 | 12/2016 | Mitra et al. |

FOREIGN PATENT DOCUMENTS

| GB | 2051354 A | * | 1/1981 | ........... G01F 1/7042 |
| WO | 2016068867 A1 | | 5/2016 | |

* cited by examiner

METHOD FOR UREA CONVERSION EFFICIENCY MEASUREMENT

CROSS-REFERENCE TO RELATED APPLICATIONS

This application claims the benefit of U.S. Provisional Application No. 62/448,425 filed on Jan. 20, 2017. The entire disclosure of the above application is incorporated herein by reference.

FIELD

The present disclosure relates to improved methods for analyzing and calibrating internal combustion engine aftertreatment systems. The disclosure particularly pertains to understanding and analyzing selective catalytic reduction of $NO_x$ by ammonia.

BACKGROUND

This section provides background information related to the present disclosure which is not necessarily prior art.

Internal combustion engines operable to combust diesel fuel have been useful as prime movers for vehicles for many years. Present diesel engine applications often require custom calibration to achieve acceptable efficiencies relative to applicable regulatory standards. In one example, an emissions regulation requires greater than 95% $NO_x$ conversion.

Development of an exhaust aftertreatment system suitable for commercial sale may require testing of one or more prototype aftertreatment systems in a laboratory environment before the engine and aftertreatment designs are finalized. During design and testing phases, it may be necessary to incorporate the use of a hot flow bench or test mule engines to obtain the target exhaust conditions and subsequently calibrate a particular diesel engine.

Many exhaust aftertreatment systems inject a diesel exhaust fluid (DEF) into the exhaust that evaporates and then converts to gaseous $NH_3$ and $CO_2$. DEF is an aqueous urea solution typically made from 32.5 wt % urea and 67.5 wt % deionized water. DEF is used as a consumable in selective catalytic reduction (SCR) in order to lower $NO_x$ concentration in the diesel exhaust emissions from diesel engines. One known commercially available DEF is commonly referred to as AdBlue™.

Analytical methods used to measure constituents in the exhaust of an internal combustion engine downstream of an aqueous urea injection system and SCR catalyst cannot discriminate between $NO_x$ originating from the engine, and $NO_x$ originating from the oxidation of urea or $NH_3$. Therefore, the development of a test method to achieve the goal of simultaneously distinguishing between $NO_x$ formed by combustion of fuel and $NO_x$ formed by oxidation of the reductant would be greatly advantageous to those practitioners of the art, through improved understanding of the chemistry and an accurate determination of the urea evaporation, conversion efficiency, and γ-UI (uniformity index) to assess overall system performance.

SUMMARY

This section provides a general summary of the disclosure, and is not a comprehensive disclosure of its full scope or all of its features.

In a first aspect of the present disclosure, there is provided a method for characterizing a chemical reaction in an exhaust after-treatment system. The method includes providing a first molecule that includes a chemical element that is isotopically labelled; injecting the isotopically labelled first molecule into an exhaust stream of the exhaust after-treatment system to supply the isotopically labelled first molecule to an exhaust treatment component; and quantifying second molecules including the chemical element that is isotopically labelled that are produced through a chemical reaction of the first molecule with other constituents of the exhaust stream.

According to the first aspect of the present disclosure, the first molecule may include at least one of ammonia having an isotope of nitrogen that is selected from the group consisting of $^{15}N$, $^{16}N$ and $^{17}N$; urea having an isotope of nitrogen that is selected from the group consisting of $^{15}N$, $^{16}N$ and $^{17}N$; urea having an isotope of carbon that is selected from the group consisting of $^{11}C$, $^{13}C$, and $^{14}C$; urea having an isotope of oxygen that is selected from the group consisting of $^{17}O$ and $^{18}O$; urea having an isotope of hydrogen that is selected from the group consisting of $^{2}H$ or $^{3}H$; and ammonia having an isotope of hydrogen that is selected from the group consisting of $^{2}H$ or $^{3}H$.

According to the first aspect of the present disclosure, the step of quantifying utilizes infrared spectroscopy, Raman spectroscopy, mass spectroscopy, nuclear magnetic resonance spectroscopy, or a combination thereof.

According to the first aspect of the present disclosure, the method may further comprise a step of distinguishing the second molecules including the chemical element that is isotopically labelled from other molecules having a naturally occurring form of the chemical element.

According to the first aspect of the present disclosure, the method may further comprise determining a urea evaporation and conversion efficiency, or determining a γ-Uniformity Index.

According to a second aspect of the present disclosure, there is provided a system for analyzing an exhaust gas, wherein the system includes a supply of an exhaust treatment fluid including a first molecule that includes a chemical element that is isotopically labelled; a delivery device for adding the exhaust treatment fluid including the first molecule that includes the chemical element that is isotopically labelled to the exhaust gas; an exhaust treatment device configured to receive the exhaust treatment fluid including the first molecule that includes the chemical element that is isotopically labelled and the exhaust gas; and a molecular analyzer positioned downstream of the exhaust treatment device that is operable to detect second molecules including the chemical element that is isotopically labelled that are produced through a chemical reaction of the first molecule with other constituents of the exhaust gas.

According to the second aspect of the present disclosure, the molecular analyzer is configured to quantify the second molecules including the chemical element that is isotopically labelled.

According to the second aspect of the present disclosure, the chemical element that is isotopically labelled is at least one selected from the group consisting of nitrogen, carbon, oxygen, and hydrogen, and the molecular analyzer is configured to differentiate the second molecules including the chemical element that is isotopically labelled from other molecules having a naturally occurring form of the chemical element.

According to the second aspect of the present disclosure, the molecular analyzer is configured to utilize infrared spectroscopy, Raman spectroscopy, mass spectroscopy, nuclear magnetic resonance spectroscopy, or a combination thereof.

According to the second aspect of the present disclosure, the first molecule may include at least one of ammonia having an isotope of nitrogen that is selected from the group consisting of $^{15}N$, $^{16}N$, and $^{17}N$; urea having an isotope of nitrogen that is selected from the group consisting of $^{15}N$, $^{16}N$ and $^{17}N$; urea having an isotope of carbon that is selected from the group consisting of $^{11}C$, $^{13}C$, and $^{14}C$; urea having an isotope of oxygen that is selected from the group consisting of $^{17}O$ and $^{18}O$; urea having an isotope of hydrogen that is selected from the group consisting of $^{2}H$ or $^{3}H$; and ammonia having an isotope of hydrogen that is selected from the group consisting of $^{2}H$ or $^{3}H$.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 7:
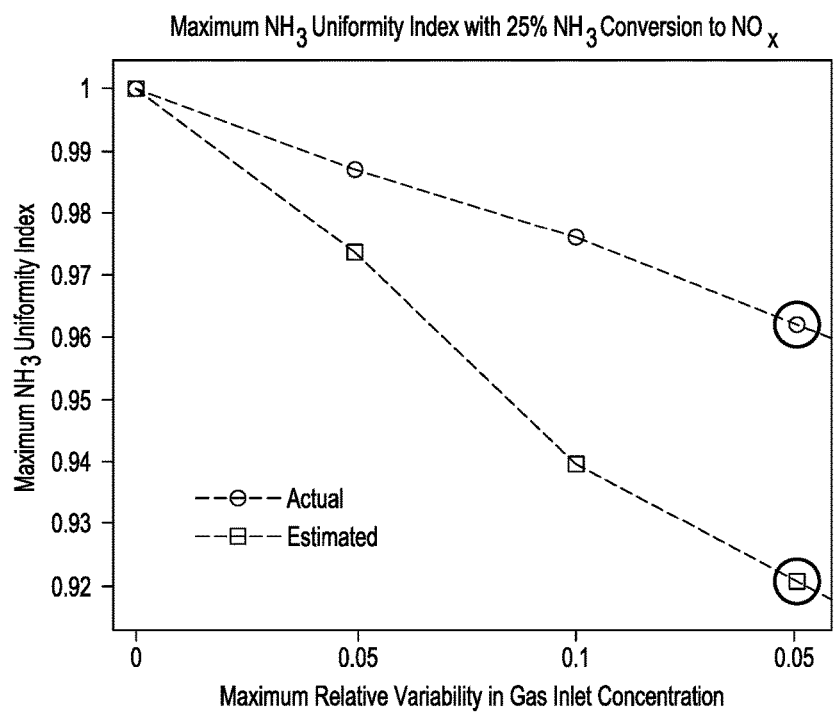
Figure 8:
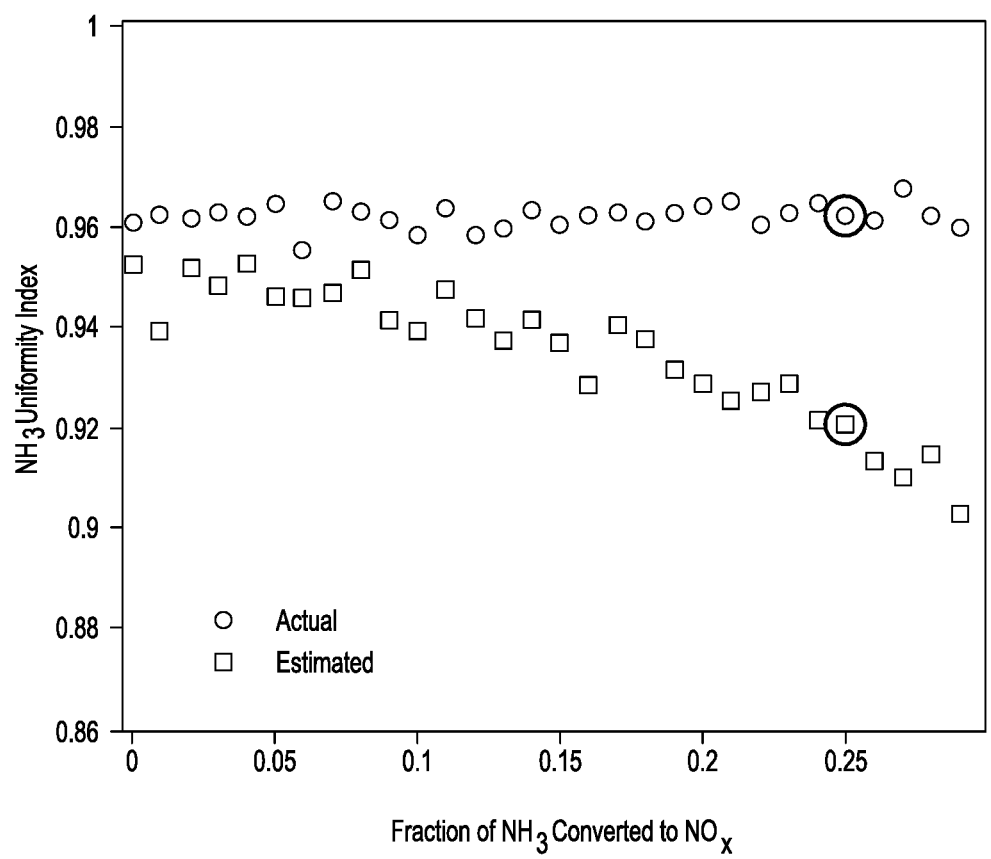

FIG. 7 is a graph that illustrates that when some partial oxidation of $NH_3$ to $NO_x$ occurs, (a) the actual γ-Uniformity Index and estimated γ-Uniformity Index only agree when there is no relative variability in gas inlet concentration at an SCR inlet, and (b) an increase in gas relative variability increases the error of the estimated γ-Uniformity Index; and FIG. 8 is a graph that illustrates that actual γ-Uniformity Index and estimated γ-Uniformity Index increases as partial oxidation of $NH_3$ to $NO_x$ increases.

Corresponding reference numerals indicate corresponding parts throughout the several views of the drawings.

DETAILED DESCRIPTION

Example embodiments will now be described more fully with reference to the accompanying drawings.

Figure 1:
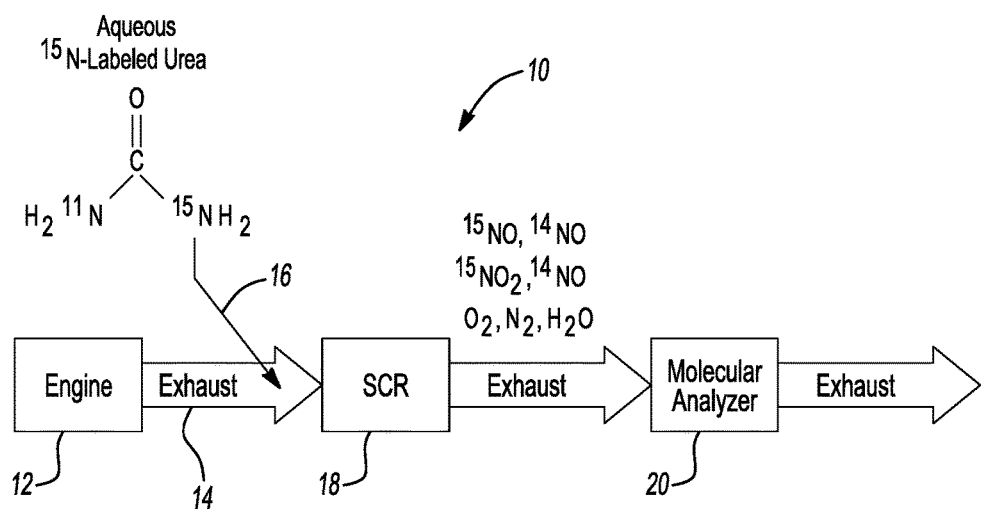
FIG. 1 is a schematic depicting an exemplary exhaust after-treatment system constructed in accordance with the teachings of the present disclosure where both engine-out $NO_x$ ($^{14}NO$ and $^{14}NO_2$) and $NO_x$ derived from a urea reagent ($^{15}NO$ and $^{15}NO_2$) that includes isotopically labelled nitrogen (N) are illustrated.

An exemplary exhaust aftertreatment system 10 is shown in FIG. 1. System 10 comprises an internal combustion engine 12, an engine exhaust passage 14, a device to introduce aqueous urea into the exhaust such as a pump and/or injector 16, an exhaust treatment component 18 including, for example, an SCR catalyst, and a molecular analyzer 20 that can identify and quantify different chemical species. Numerous other components could be included in the system, such as a device to introduce gaseous ammonia instead of aqueous urea, a diesel oxidation catalyst, a diesel particulate filter, a passive $NO_x$ adsorber, a SCR-coated DPF, an ammonia slip catalyst, a mixer, a burner (thermal unit) and the like. It is also possible that the molecular analyzer 20 be designed to sample only a portion of the total exhaust stream, and not the entire gas stream, as implied by the simple schematic in FIG. 1.

According to the present disclosure, the molecular analyzer 20 is configured to distinguish chemical compounds having different molecular weights and/or vibrational spectra. While isotopically labelled elements have been used in the medical and food processing industries, these elements have not before been used in the development of exhaust after-treatment systems. For example, in order to distinguish $NO_x$ that originates from the engine 12 and $NO_x$ that originates from the oxidation of urea or $NH_3$, the aqueous urea solution includes a different isotope of nitrogen (N) than that which typically occurs in nature. In other words, the nitrogen is isotopically labeled. In this regard, most naturally occurring nitrogen has an atomic mass of fourteen ($^{14}N$). Accordingly, in order to distinguish $NO_x$ that originates from the engine 12 and $NO_x$ that originates from the oxidation of urea or $NH_3$, the aqueous urea solution includes an isotope of nitrogen having an atomic mass of that is different from that which most often occurs naturally (e.g., $^{15}N$, $^{16}N$, or $^{17}N$) such that the amount of $NO_x$ that originates from the oxidation of the urea aqueous solution can be easily distinguished by molecular analyzer 20.

Specifically, molecular analyzer 20 is configured to distinguish between $^{14}N$- and $^{15}N$-containing molecules, such as $^{14}NO$ and $^{15}NO$. It should be understood, however, that different isotopes of nitrogen (e.g., $^{16}N$ or $^{17}N$) can be used without departing from the spirit and scope of the present disclosure. Note that while $^{15}N$ may be a naturally occurring isotope of nitrogen, the amount of this isotope that occurs naturally is so small (i.e., 0.364%) that any amount of this isotope that is present in the exhaust passage 14 along with the isotopically labelled nitrogen should not significantly affect the determination of whether $NO_x$ in the exhaust passage 14 originated from the engine 12 or from the oxidation of urea or $NH_3$. Notwithstanding, molecular analyzer 20 can be configured to correct for this small percentage, or another analytical device can be used to correct for this small percentage. Regardless, by distinguishing $NO_x$ that originates from the engine 12 and $NO_x$ that originates from the oxidation of urea or $NH_3$, the exhaust after-treatment system design and efficiency for engine-out $NO_x$ reduction can be improved.

More particularly, during design of a diesel exhaust after-treatment system, the "urea evaporation and conversion efficiency" is calculated to determine whether the design can optimally function to properly treat the engine exhaust. This efficiency is intended to be a measure of the extent to which urea [CO(NH$_2$)$_2$] in the aqueous urea solution evaporates and then converts to gaseous NH$_3$ by the following reactions:

$$\text{Thermolysis: } CO(NH_2)_{2(g)} \rightarrow HNCO_{(g)} + NH_{3(g)} \quad \{1\}$$

$$\text{Hydrolysis: } HNCO_{(g)} + H_2O_{(g)} \rightarrow NH_{3(g)} + CO_{2(g)} \quad \{2\}$$

An equation for calculation of the minimum urea evaporation and conversion efficiency (ε) is as follows:

$$\varepsilon = \left(\frac{1}{340251.8}\right)\left(\frac{\dot{m}_{exhaust}\Delta C_N}{f}\right) \quad \{3\}$$

where:
$\dot{m}_{exhaust}$ is engine exhaust flow rate (g/s);
f is the DEF injection flow rate (mL/s); and
$\Delta C_N$ is the net concentration change (inlet-outlet) of N-containing species (ppmv), represented by:

$$\Delta C_N = x\Delta C_{NO} + x\Delta C_{NO_2} - 2\Delta C_{N_2O} - \Delta C_{NH_3} - \Delta C_{HNCO} \quad \{4\}$$

where x=NH$_3$/NO$_x$ is the reaction stoichiometry and typically x=1 (as a conservative limit) based on reaction stoichiometry for fast and standard SCR (it is not equivalent to the ratio of injected NH$_3$ to NO$_x$):

$$4NO + 4NH_3 + O_2 \rightarrow 4N_2 6H_2O \quad \{5\}$$

$$NO + NO_2 + 2NH_3 \rightarrow 2N_2 + 3H_2O \quad \{6\}$$

However, there are some potential biases to equation {4}. First, the reaction stoichiometry for NO$_x$ reduction isn't always equal to x=1:

$$6NO_2 + 8NH_3 \rightarrow 7N_2 + 12H_2O \quad x=1.3 \quad \{7\}$$

$$2NO_2 + 4NH_3 + O_2 \rightarrow 3N_2 6H_2O \quad x=2.0 \quad \{8\}$$

Second, NH$_3$ can oxidize at elevated exhaust temperatures in the gas phase or on the surface of different components in the after-treatment system, such as a mixer, SCR catalyst, or ammonia-slip catalyst, to form NO$_x$ or N$_2$ independent of reaction with engine-out NO$_x$:

$$4NH_3 + 5O_2 \rightarrow 4NO + 6H_2O \quad \{9\}$$

$$4NH_3 + 7O_2 \rightarrow 4NO_2 + 6H_2O \quad \{10\}$$

Figure 2:
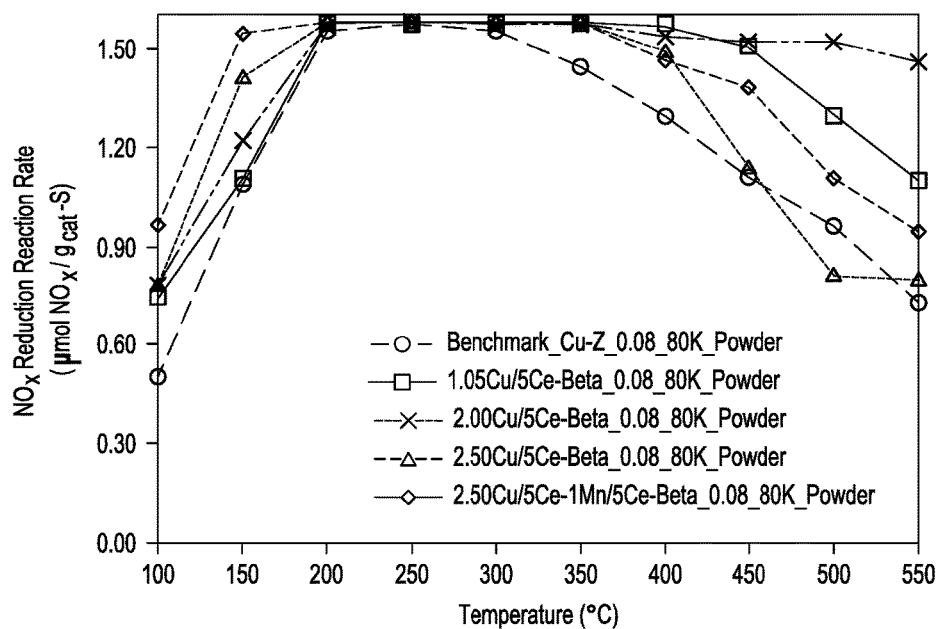
FIG. 2 is a graph depicting an apparent decrease in $NO_x$ conversion (reaction rate) at elevated catalyst temperatures for a series of catalysts.

In experimental data, the direct oxidation of NH$_3$ to NO$_x$ typically occurs on the surfaces of SCR catalysts at temperatures exceeding 250° C. and is revealed as an apparent decrease in observed NO$_x$ conversion, as shown in FIG. 2. Described another way, as NH$_3$ passes through the SCR catalyst component 18, the NO$_x$ level in exhaust is reduced, but at elevated temperatures some of the NH$_3$ will be oxidized which causes an increases the NO$_x$ levels of the exhaust.

Figure 3:
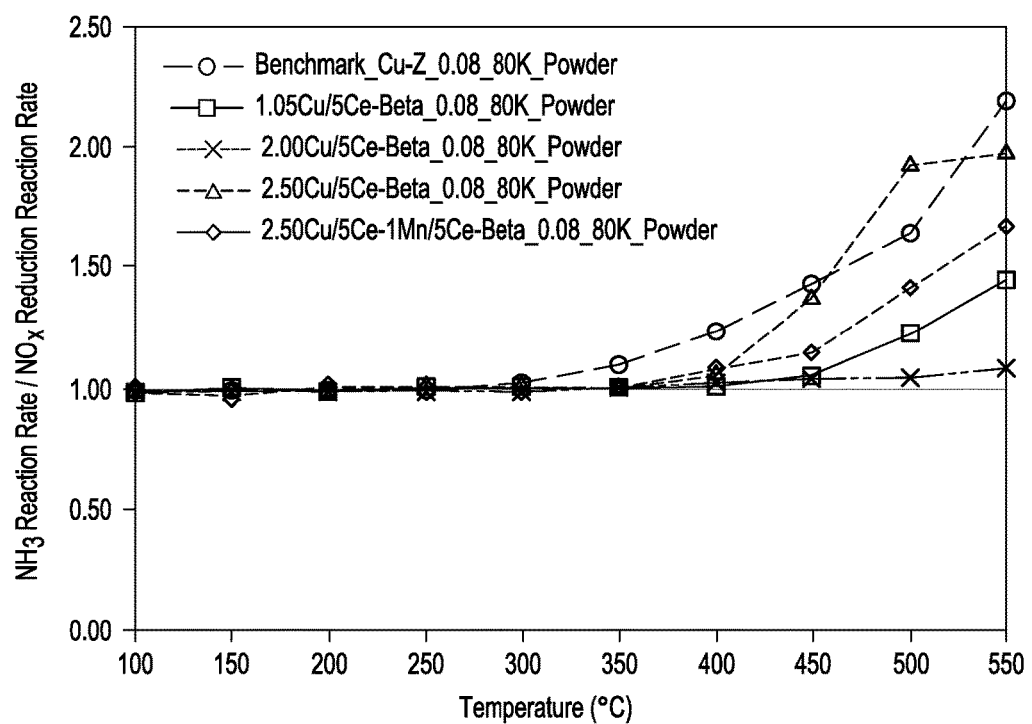
FIG. 3 is a graph depicting relative rates of $NH_3$ and $NO_x$ conversion with increasing temperature for the same series of catalysts shown in FIG. 2.

During the operating conditions in which the apparent NO$_x$ conversion rate is decreasing, the relative rate of NH$_3$ conversion is increasing, as shown in FIG. 3. In reality, the rate of NO$_x$ reduction by NH$_3$ continues to increase with increasing temperature, but the relative rate of NH$_3$ oxidation to NO$_x$ increases faster with increasing temperature (it has a higher activation energy), so the observed NO$_x$ conversion is actually a net conversion resulting from NO$_x$ disappearance (via reduction) and formation (via NH$_3$ oxidation to NO$_x$). The consequence of NH$_3$ oxidation to NO$_x$ on the calculated value of ε can be dramatic, as described below in Example 1.

Figure 4:
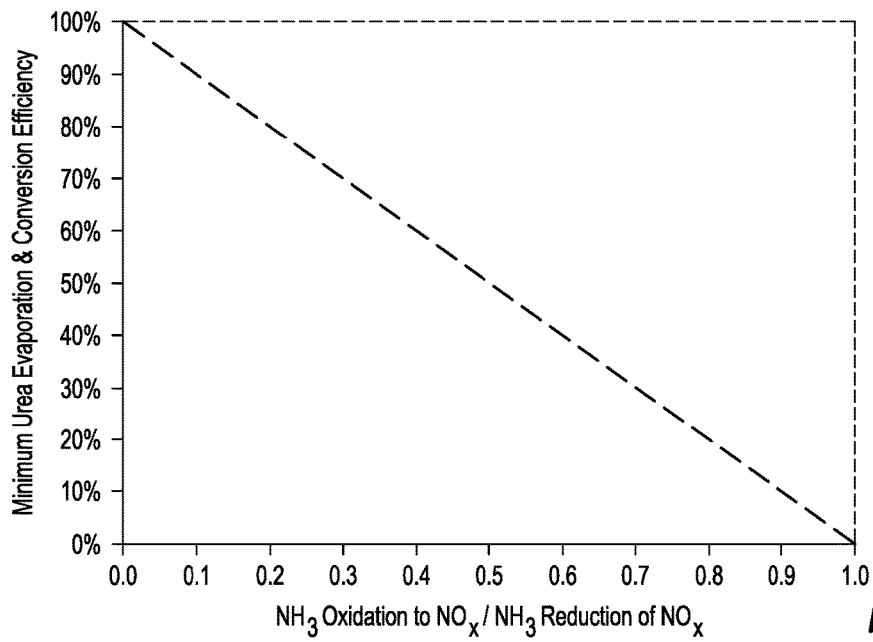
FIG. 4 is a graph depicting the impact of $NH_3$ oxidation to $NO_x$ on the calculated value of $\varepsilon$.

Example 1: With reference to FIG. 4, consider the following baseline, simplified case:

Engine exhaust flow rate=52 g/s
DEF flow rate=0.2052 mL/s
100% urea conversion to $^{14}$NH$_3$ with no intermediate products (such as HNCO)
1343.1 ppmv $^{14}$NH$_3$ in the exhaust upstream of the SCR catalyst
1343.1 ppmv $^{14}$NO in the exhaust upstream of the SCR catalyst
50% $^{14}$NH$_3$-$^{14}$NO conversion to N$_2$
0% $^{14}$NH$_3$ partial oxidation to $^{14}$NO$_x$ In this baseline case, the calculated urea evaporation and conversion efficiency=1.00 (or 100%). As the last of the seven conditions changes (i.e., as the extent to which $^{14}$NH$_3$ partial oxidation to $^{14}$NO$_x$ increases), the calculated value of ε decreases significantly, as there is no means for differentiation between $^{14}$NO$_x$ originating from the engine and $^{14}$NO$_x$ originating from $^{14}$NH$_3$ oxidation.

Thus, as noted above, the present disclosure provides a method and system that utilizes isotopically labeled N in ammonia or an ammonia precursor such as urea to differentiate N-species originating from fuel combustion in the engine from species derived from the chemical conversion of urea or ammonia (i.e., the method is useful for SCR systems that utilize either urea, ammonia, other reductants that generate ammonia, or a combination thereof). In their natural form, the common (most abundant) elements in urea exhaust treatment fluid are $^{12}$C, $^{14}$N, $^{16}$O, and $^{1}$H. In contrast, if N in the urea or ammonia is an isotope (e.g., $^{15}$N), then $^{15}$N can be followed to gain better insight into the reactions that take place. That is, molecules such as $^{15}$NO and $^{15}$NO$_2$ that result from the oxidation of urea or NH$_3$ can be differentiated from molecules such as $^{14}$NO and $^{14}$NO$_2$ that are produced during engine combustion. Other examples include differentiating $^{15}$N$_2$O and $^{15}$N$^{14}$NO from $^{14}$N$_2$O, et cetera. In addition, with the appropriate analytical method, it is even possible to close the N material balance by measurement of $^{14}$N$^{15}$N and $^{15}$N$^{15}$N.

When using isotopically labeled nitrogen ($^{15}$N), the equation for ε remains unchanged; however, equation {4} needs to be updated:

$$\Delta C_N = x\Delta C_{14NO} + x\Delta C_{14NO_2} - \Delta C_{15NO} - \Delta C_{15NO_2} - 2\Delta C_{14N_2O/15N_2O/14N15NO} - \Delta C_{15NH_3} - \Delta C_{H15NCO} \quad \{11\}$$

Note that this equation does not take into account N$_2$ in the overall N-balance (though that in principle could be done if needed and the chosen analytical method is capable of molecule discrimination and quantification). However, simple use of $^{15}$N-labeled urea or ammonia is not sufficient. An analytical method must be developed to enable facile identification and quantification of $^{14}$N- and $^{15}$N-chemical species in the presence of molecules commonly found in the exhaust of diesel-based internal combustion engines, including H$_2$O, CO, CO$_2$, N$_2$, O$_2$, and various hydrocarbons. Various analytical methods are suitable for identification and quantification of chemical species by molecular analyzer 20 include mass spectroscopy, infrared spectroscopy, Raman spectroscopy, or a combination thereof. Other methods could be identified by those skilled in the art; however, spectroscopic methods that take advantage of the shift in reduced mass of vibrational modes in each molecule as a consequence of changing the atom nucleus are preferred.

Molecules absorb specific frequencies of light that are characteristic of their structure (bonds between atoms), called resonant frequencies. The vibration in molecular bonds can be described by simple harmonic motion with a force constant (k), in which case the frequency (v) is a function of the reduced mass of the atoms in the bond (μ). The following is a simplification:

$$v = \frac{1}{2\pi}\sqrt{\frac{k}{m}} \quad \{12\}$$

Thus, the increased atomic mass of the $^{15}N$ will in general reduce the resonant frequency of a bond or molecular motion, allowing differentiation between $^{15}N$ and $^{14}N$ compounds by molecular analyzer 20. Other atoms in urea instead of nitrogen could also be isotopically labeled to achieve similar objectives, such as carbon (C) or hydrogen (H). In the case of carbon, differentiation between $^{14}CO/^{14}CO_2$, $^{12}CO/^{12}CO_2$, $HN^{12}CO$ and $HN^{14}CO$ could also enable a facile means for direct measurement of urea conversion and operando measurement of the rate of urea deposit formation.

Figure 5:
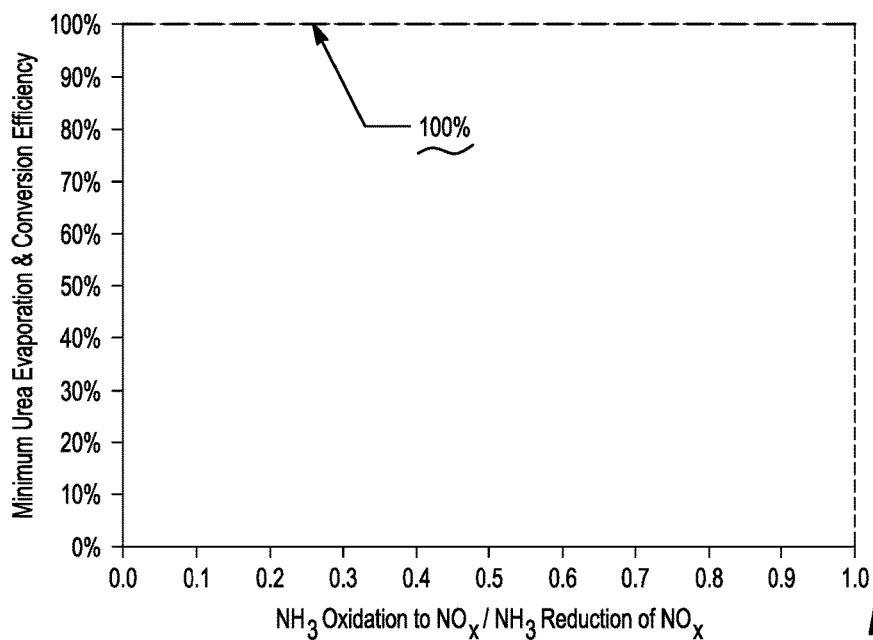
FIG. 5 is a graph depicting the lack of impact of $NH_3$ oxidation to $NO_x$ on the experimental value of urea evaporation and conversion efficiency for a system shown in FIG. 1.

By isotopically labelling specific chemical elements of the exhaust treatment fluid, the present disclosure enables the correct determination of urea evaporation and conversion efficiency. With reference to FIG. 5, consider the following baseline case:
  Engine exhaust flow rate=52 g/s
  DEF flow rate=0.2052 mL/s
  100% urea conversion to $^{15}NH_3$ with no intermediate products (such as $H^{15}NCO$)
  1343.1 ppmv $^{15}NH_3$ in the exhaust upstream of the SCR catalyst
  1343.1 ppmv $^{14}NO$ in the exhaust upstream of the SCR catalyst
  50% $^{15}NH_3$-$^{14}NO$ conversion to $N_2$
  0% $^{15}NH_3$ partial oxidation to $^{15}NO_x$ In this baseline case, the calculated urea evaporation and conversion efficiency=1.00 (or 100%). As the extent to which $^{15}NH_3$ partial oxidation to $^{15}NO_x$ increases, the calculated value of ε remains at 1.00 (the correct value), as the invention enables differentiation between $^{14}NO_x$ and $^{15}NO_x$. This is in noticeable contrast to the situation observed in laboratories worldwide today, as shown in FIG. 4, which demonstrate a significant decrease in the calculated value of ε as the rate of ammonia oxidation to $NO_x$ increases. That is, the present disclosure eliminates the bias from temperature dependent $NH_3$ oxidation to $NO_x$. As a result, more efficient exhaust after-treatment systems can be developed.

Further, the present disclosure is useful for characterizing or calibrating different after-treatment subsystems to the specific real world conditions of the engine. This characterization or calibration could involve optimizing SCR volume or formulation, injector reductant flow rates and/or orientation, mixer shapes and/or orientation, use of a post SCR reductant slip catalyst (ASC), and $NH_3$ Uniformity Index (γ-Uniformity Index).

Figure 6:
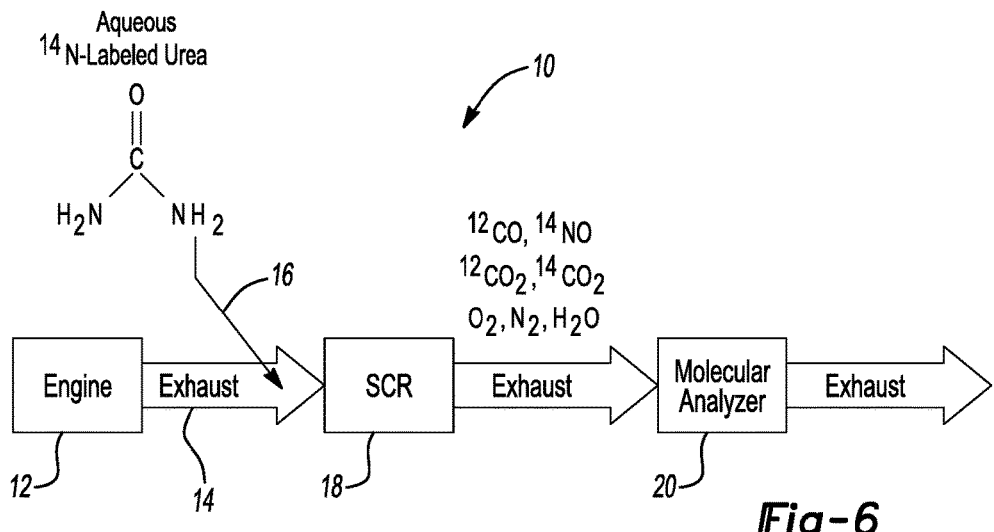
FIG. 6 is a schematic depicting an alternate system for analyzing the exhaust gas where carbon (C) is isotopically labelled such that molecules ($^{14}CO$ and $^{14}CO_2$) produced through oxidation of the urea can be distinguished from engine-out $CO_x$ ($^{12}CO$ and $^{12}CO_2$)

FIG. 6 illustrates another embodiment of the invention, in which $^{14}C$-labeled urea is used instead of $^{15}N$-labeled urea. Other isotopic labels, or a combination thereof, are also possible.

As noted above, isotopically modifying a chemical constituent during design of a diesel exhaust after-treatment system can also be useful for determining the "γ-Uniformity Index," which is a measure of flow uniformity that is calculated to determine whether the design can optimally function to properly treat the engine exhaust. Similar to conversion efficiency, the measurement of γ-UI is likewise biased by the oxidation of $NH_3$ to $NO_x$. To facilitate quantification of this effect, a program was created using software such as, for example, MATLAB to generate a distribution of $NH_3$ at the inlet of SCR catalyst 18 in which both $NH_3$ SCR and $NH_3$ partial oxidation to $NO_x$ could occur, and the actual γ-UI (which takes into account $NH_3$ partial oxidation) was compared with the estimated γ-UI (which ignores $NH_3$ partial oxidation, as is done experimentally today in the absence of the invention disclosed herein). The entire procedure is as follows:

A function was defined:
  NH3UniformityIndexandConversion_Function.m
    Input parameters for the function were defined as follows:
      N=# of γ-UI Map/Measurement Locations (e.g., 68 is typical)
      Baseline mean $NH_3$ Concentration upstream of the SCR (e.g., 600 ppmv)
      Baseline mean $NO_x$ Concentration upstream of the SCR (e.g., 600 ppmv)
      The maximum variation in upstream gas concentration as a percent of the baseline
      The SCR conversion efficiency (e.g., 98%)
      The fraction of $NH_3$ partially oxidized to $NO_x$ (e.g., 7%)
    The following script calculation procedure was used:
      (1) A distribution of $NH_3$ and $NO_x$ values at the SCR inlet are created from user input parameters using the rand function (a random # generator)
      (2) Re-calculate the mean inlet $NH_3$ and $NO_x$ concentrations based on the output of (1).
      (3) At each of the N map locations two simple chemistry calculations are made:
        $NH_3$ partial oxidation to $NO_x$ (based on user defined input)
        $NH_3$ reduction of $NO_x$ (the SCR conversion efficiency is applied to the limiting reagent, as variability in $NH_3$ and $NO_x$ concentrations at the inlet can lead to a range of $NH_3$:$NO_x$ from <1 to >1).
      (4) At each of the N map locations the outlet $NO_x$ and $NH_3$ concentrations are calculated from the results of (3).
      (5) Calculate mean $NH_3$ and $NO_x$ conversion from the mean inlet and outlet concentrations.
      (6) Calculate the actual γ-UI for $NH_3$ based on the output of (1) (i.e., the actual inlet $NH_3$ concentrations at each location):

$$\gamma - UI = 1 - \sum_{i=1}^{N} \frac{\sqrt{(C_{mean} - C_{inlet,i})^2}}{2NC_{mean}} \quad \{13\}$$

(7) Calculate the estimated γ-UI for $NH_3$ using equation {13} and estimates of the NH3 concentration at the inlet of the SCR based on the following formula {14} (all concentrations refer to $NH_3$ except where noted otherwise):

$$C_{inlet,i} = C_{outlet,i} + (C_{mean\ inlet\ NOx} - C_{outlet\ NOx,i}) \quad \{14\}$$

A typical output of the MATLAB code is shown in FIG. 7, which demonstrates that when some partial oxidation of $NH_3$ to $NO_x$ occurs, (a) the actual γ-UI and estimated γ-UI only agree when there is no relative variability in gas inlet concentration at the SCR inlet, and (b) an increase in gas relative variability increases the error of the estimated γ-UI. In FIG. 7, actual γ-UI and estimated γ-UI at the inlet of a SCR catalyst were calculated using N=68, baseline [NO$_x$]$_{inlet}$=baseline [NH$_3$]$_{inlet}$=600 ppmv, SCR Conversion Efficiency (of the limiting reagent)=98%, 25% of NH$_3$ converts to NO$_x$. Maximum Relative Variability is a percentage relative to the mean that defines the range in concentrations observed at the inlet. For example, if Maximum Relative Variability=0.1 (10%) and [NH$_3$]$_{inlet}$=600 ppmv, the minimum concentration allowed at the inlet=90%×600=540 ppmv, and the maximum concentration allowed at the inlet=110%×600=660 ppmv. Data points circled in red are identical to those likewise circled on FIG. 8.

Alternatively, simulations demonstrate that for a fixed Maximum Relative Variability in Gas Inlet Concentration, the gap between actual γ-UI and estimated γ-UI increases as partial oxidation of NH$_3$ to NO$_x$ increases (FIG. 8). In FIG. 8, actual γ-UI and estimated γ-UI at the inlet of a SCR catalyst as a function of NH$_3$ conversion to NO$_x$ using N=68, baseline [NO$_x$]$_{inlet}$=baseline [NH$_3$]$_{inlet}$=600 ppmv, SCR Conversion Efficiency (of the limiting reagent)=98%, Maximum Relative Variability=0.15 (15%). Data points circled in red are identical to those likewise circled on FIG. 7. In practical terms, it is possible for experimental, estimated γ-UI measurements to be less than the actual γ-UI. In these cases, due to the error introduced by NH$_3$ oxidation, additional experiments are conducted and perhaps system components related to DEF spray and mixing are redesigned, thus adding time and cost to the overall system design, validation and test program. By isotopically labeling a chemical constituent, however, the added time and cost when developing a suitable exhaust after-treatment system can be avoided.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

For example, one skilled in the art will recognize that during periods of time in which there is no dosing of reductant, there may nevertheless be ammonia stored on a catalyst, or a solid deposit within the system derived from urea, deposited during an earlier reductant dosing event. During certain operational transients, such as an increase in temperature, these moieties could oxidize and/or hydrolyze, yielding NO$_x$ species. If the ammonia and urea-derived moieties comprised an isotopic label, then it would be possible to distinguish generated NO$_x$ from these moieties from NO$_x$ in the engine exhaust.

What is claimed is:

1. A method for characterizing a chemical reaction in an exhaust after-treatment system, comprising:
   providing a first molecule of urea or ammonia that includes a chemical element that is isotopically labelled;
   injecting the isotopically labelled first molecule into an exhaust stream of the exhaust after-treatment system to supply the isotopically labelled first molecule to an exhaust treatment component; and
   quantifying second molecules including the chemical element that is isotopically labelled that are produced through a chemical reaction of the first molecule with other constituents of the exhaust stream.

2. The method of claim 1, wherein the first molecule includes ammonia having an isotope of nitrogen that is selected from the group consisting of $^{15}$N, $^{16}$N, and $^{17}$N.

3. The method of claim 1, wherein the first molecule includes urea having an isotope of nitrogen that is selected from the group consisting of $^{15}$N, $^{16}$N, and $^{17}$N.

4. The method of claim 1, wherein the first molecule includes urea having an isotope of carbon that is selected from the group consisting of $^{11}$C, $^{13}$C, and $^{14}$C.

5. The method of claim 1, wherein the first molecule includes urea having an isotope of oxygen that is selected from the group consisting of $^{17}$O and $^{18}$O.

6. The method of claim 1, wherein the first molecule includes urea having an isotope of hydrogen that is selected from the group consisting of $^2$H or $^3$H.

7. The method of claim 1, wherein the first molecule includes ammonia having an isotope of hydrogen that is selected from the group consisting of $^2$H or $^3$H.

8. The method of claim 1, wherein the quantifying utilizes infrared spectroscopy, Raman spectroscopy, mass spectroscopy, nuclear magnetic resonance spectroscopy, or a combination thereof.

9. The method of claim 1, further comprising distinguishing the second molecules including the chemical element that is isotopically labelled from other molecules having a naturally occurring form of the chemical element.

10. The method of claim 9, wherein the first molecule is urea and the method further comprises determining a urea evaporation and conversion efficiency, or determining a γ-Uniformity Index.

11. A system for analyzing an exhaust gas, comprising:
   a supply of an exhaust treatment fluid including a first molecule of urea or ammonia that includes a chemical element that is isotopically labelled;
   a delivery device for adding the exhaust treatment fluid including the first molecule that includes the chemical element that is isotopically labelled to the exhaust gas;
   an exhaust treatment device configured to receive the exhaust treatment fluid including the first molecule that includes the chemical element that is isotopically labelled and the exhaust gas; and
   a molecular analyzer positioned downstream of the exhaust treatment device that is operable to detect second molecules including the chemical element that is isotopically labelled that are produced through a chemical reaction of the first molecule with other constituents of the exhaust gas.

12. The system of claim 11, wherein the molecular analyzer is configured to quantify the second molecules including the chemical element that is isotopically labelled.

13. The system of claim 12, wherein the chemical element that is isotopically labelled is at least one selected from the group consisting of nitrogen, carbon, oxygen, and hydrogen, and the molecular analyzer is configured to differentiate the second molecules including the chemical element that is isotopically labelled from other molecules having a naturally occurring form of the chemical element.

14. The system of claim 11, wherein the molecular analyzer is configured to utilize infrared spectroscopy, Raman spectroscopy, mass spectroscopy, nuclear magnetic resonance spectroscopy, or a combination thereof.

15. The system of claim 11, wherein the first molecule includes ammonia having an isotope of nitrogen that is selected from the group consisting of $^{15}$N, $^{16}$N, and $^{17}$N.

16. The system of claim 11, wherein the first molecule includes urea having an isotope of nitrogen that is selected from the group consisting of $^{15}$N, $^{16}$N, and $^{17}$N.

17. The system of claim 11, wherein the first molecule includes urea having an isotope of carbon that is selected from the group consisting of $^{11}C$, $^{13}C$, and $^{14}C$.

18. The system of claim 11, wherein the first molecule includes urea having an isotope of oxygen that is selected from the group consisting of $^{17}O$ and $^{18}O$.

19. The system of claim 11, wherein the first molecule includes urea having an isotope of hydrogen that is selected from the group consisting of $^{2}H$ or $^{3}H$.

20. The system of claim 11, wherein the first molecule includes ammonia having an isotope of hydrogen that is selected from the group consisting of $^{2}H$ or $^{3}H$.

* * * * *